(12) United States Patent
Rucker et al.

(10) Patent No.: US 6,947,150 B2
(45) Date of Patent: Sep. 20, 2005

(54) METHOD AND APPARATUS FOR DETERMINING OUT-OF-PLANE DEFECTS IN A PAPER SAMPLE

(75) Inventors: Kevin S. Rucker, Burbank, WA (US); Guy W. Leolich, International Falls, MN (US); Matthew F. Wannamaker, Brush Prairie, WA (US); Edward J. Mettler, International Falls, MN (US)

(73) Assignee: Boise White Paper, LLC, Boise, ID (US)

( * ) Notice: Subject to any disclaimer, the term of this patent is extended or adjusted under 35 U.S.C. 154(b) by 226 days.

(21) Appl. No.: 10/324,206

(22) Filed: Dec. 19, 2002

(65) Prior Publication Data

US 2003/0214648 A1 Nov. 20, 2003

Related U.S. Application Data

(60) Provisional application No. 60/381,454, filed on May 16, 2002.

(51) Int. Cl.$^7$ .............................................. G01B 11/30
(52) U.S. Cl. ........................ 356/600; 356/429; 356/446
(58) Field of Search .......................... 356/237.1, 237.2, 356/238.1, 600, 446, 429–431; 250/559.45, 559.46

(56) References Cited

U.S. PATENT DOCUMENTS

| | | | |
|---|---|---|---|
| 4,184,082 A | * | 1/1980 | Peoples ...................... 356/446 |
| 4,617,682 A | | 10/1986 | Mori et al. |
| 4,760,271 A | | 7/1988 | Brenholdt |
| 4,878,114 A | * | 10/1989 | Huynh et al. ............... 382/108 |
| 5,243,407 A | | 9/1993 | King et al. |
| 5,614,662 A | | 3/1997 | Hallan et al. |
| 5,654,799 A | | 8/1997 | Chase et al. |
| 5,684,707 A | | 11/1997 | Rogowski |
| 5,726,748 A | * | 3/1998 | Morris ..................... 356/237.2 |
| 5,745,365 A | | 4/1998 | Parker |
| 5,854,683 A | | 12/1998 | Keane |
| 5,899,959 A | * | 5/1999 | Shields et al. ........... 356/237.1 |
| 6,188,077 B1 | | 2/2001 | Lind |
| 6,219,141 B1 | | 4/2001 | Perrault |
| 6,266,437 B1 | * | 7/2001 | Eichel et al. ............... 356/430 |
| 6,301,373 B1 | | 10/2001 | Bernié et al. |
| 6,335,982 B1 | * | 1/2002 | Arai et al. .................. 356/600 |

OTHER PUBLICATIONS

KODAK: EDAS 290, URL:http://www.kodakkorea.co.kr/US/en/health/scientific/products/edas290upgrade/icUPgrade.shtm (accessed on Apr. 18, 2002).

(Continued)

Primary Examiner—Richard A. Rosenberger
(74) Attorney, Agent, or Firm—Klarquist Sparkman, LLP

(57) ABSTRACT

A method and apparatus for determining out-of-plane defects in a paper sample are described. One embodiment of the method includes providing a paper sample, illuminating the sample with light, determining light scattering resulting from the light at a plurality of measuring regions, and determining an out-of-plane defect value by assigning the measuring regions to plural bands, calculating a standard deviation of light scattering for each of the bands, and averaging standard deviations of the bands. An alternative embodiment further includes assigning the measuring regions to plural columns of the sample, determining the out-of-plane defect value for each of the columns, and calculating the median of the out-of-plane defect values of the columns. The average out-of-plane defect value may also be calculated. One embodiment of the apparatus includes a housing for excluding ambient light and for holding a paper sample, a light source, and an image-capturing device.

50 Claims, 8 Drawing Sheets

OTHER PUBLICATIONS

"Paper web inspection with intelligent line scan cameras," *Machine Vision News*, vol. 6 2000 URL:http://www.automaatioseura.fi/jaostot/mvn/mvn6/paperweb.html (accessed on Apr. 18, 2002).

Mitsubishi Paper Mills Limited, URL:http://web.infoweb.ne.jp/mpm/eng/kaihatu/software1-e.html (accessed on Apr. 18, 2002).

Paper Characterization, URL:http://www-ismv.ic.ornl.gov/projects/papercharac.htm (accessed on Apr. 18, 2002).

Huynh et al., "A New Optical Method for the Measurement of Roughness of Paper Surfaces," *Proceedings of the SID*, vol. 28, No. 4, pp. 471–475 (1987).

Luk et al., "A Vision System for In–Process Surface Quality Assessment," *Proceedings of Vision '87 Conf.*, pp. 12–43–12–58 (1987).

Luk et al., "Application of spatial spectral analysis to in–line machine inspection of surface roughness," *Proceedings of the IXth ICPR Conf.*, vol. 1, pp. 147–157 (1988).

Luk et al., "Measurement of surface roughness by a machine vision system," *J. Phys. E: Sci. Instrum.*, vol. 22, pp. 977–980 (1989).

* cited by examiner

METHOD AND APPARATUS FOR DETERMINING OUT-OF-PLANE DEFECTS IN A PAPER SAMPLE

CROSS REFERENCE TO RELATED PATENT APPLICATION

This application claims the benefit of U.S. provisional patent application No. 60/381,454, filed May 16, 2002, which is incorporated herein by reference.

FIELD

The disclosed embodiments of the method and apparatus pertain to determining out-of-plane defects on a surface, particularly a paper sample.

BACKGROUND

Modern paper manufacturing involves a complex series of mechanical and chemical processes that converts wood pulp into a finished paper product. During the manufacturing process, papermaking fibers formed from wood pulp are distributed along a moving wire screen and eventually are formed and pressed into a continuous sheet of fibers referred to as a "paper web." The paper web is further processed by elaborate drying and pressing processes to reduce the moisture in the web and form bonds between the fibers. Once dried, various surface treatments may be applied to the web, depending on the application for which the paper is ultimately used. This complex procedure requires precision control and oversight to create high quality paper products. Accordingly, paper manufacturers are constantly looking for new and improved methods of measuring and assessing the characteristics of the paper formed in their manufacturing facilities.

One important characteristic of paper is how flat its surface is after manufacture. Defects resulting from various manufacturing processes create raised or depressed regions that diverge from the plane parallel to the paper surface. These defects are referred to as "out-of-plane defects" and have a height that deviates from the average levelness of a flat sheet. There are a number of out-of-plane defects recognized by the paper industry. For instance, a "streak" appears as a sinuous line of variable length that typically appears on paper in the direction of the paper web's movement (i.e., the machine direction). Although streaks may be straight, they often wander to some degree in the direction transverse to the direction of the paper web (i.e., the cross direction). "Puckers," appear as small semi-circular raised areas on the surface of the paper, whereas "cockles" appear as waves in the plane of the paper surface.

Several techniques have been developed to analyze various paper characteristics. Few are capable of measuring out-of-plane defects and no known technique allows for an entire paper sample to be evaluated quickly and easily.

For instance, U.S. Pat. No. 5,243,407 to King et al. discloses a device for characterizing the formation of a sheet of paper, where "formation" is defined as "the manner in which fibers forming a paper sheet are distributed, disposed and intermixed within the sheet." Col. 1, lns. 48–41. The device includes a basis weight sensor "for accurately measuring local variations in the basis weight of a sheet of paper," where the sensor includes a light beam source "disposed on one side of the sheet" and a receiver "disposed on the other side of the sheet opposing the light beam source." Col. 3, lns. 48–52.

U.S. Pat. No. 5,899,959 to Shields et al. discloses an apparatus for determining visual characteristics of a paper web including "formation, moisture streaks, wire marks, dirt, roughness, coating uniformity, gloss variation, and misregister in printing." Col. 1, lns. 7–9. The apparatus includes a strobe "positioned to illuminate a section of the first surface of the paper web during each flash," and an array camera "positioned adjacent the second surface to receive the transmitted light." Col. 3, lns. 34–36, 39–40. The visual characteristics are then measured based on "the distribution of transmitted light" through the paper web. Col. 3, lns. 52–53.

U.S. Pat. No. 6,301,373 B1 to Bernie et al. discloses a similar method of determining a quality of sheet material by obtaining "scale of formation information," where formation is defined as "the local nonuniformity of sheet structure." Col. 6, lns. 41–45. The scale of formation information is determined using a "visible light transmission technique," which involves acquiring an image from a sheet placed on a lightbox. Col. 6, lns 3–5.

The referenced patents all concern measuring paper characteristics through transmitted, not reflected, light. Further, the patents concern the detection of formation, not out-of-plane, defects.

U.S. Pat. No. 4,878,114 to Huynh et al. discloses a "method for assessing the roughness of planar surfaces of manufactured products." Col. 2, lns. 6–8. The disclosed method may also be used to detect the roughness of paper surfaces and to detect surface flaws. Col. 4, lns. 28–59; Col. 5, lns. 10–17. In the disclosed invention, "[a]n area of the surface whose roughness is to be assessed is illuminated by a light source, and the reflected light is directed to the lens of a video camera. The analog output of the video camera is digitized, and the digital signal is provided to a processor which performs an analysis to provide a parameter indicative of the roughness of the surface." Col. 2, lns. 13–19. In the preferred embodiment, the reflected light is directed to the lens through microscope optics. Col. 2, lns. 67–68. The analysis performed includes obtaining "a histogram of the frequency distribution of the grey levels of the digitized image" and determining a "roughness parameter R" equal to the standard deviation divided by the root-mean-square of the measured grey-levels. Col. 3, lns. 32–45. Further, surface flaws may be detected because they cause the "skewness of the histogram to decrease from a slightly positive value to a negative value." Col. 4, lns. 46–48. Thus, "one can check the presence of the surface flaws by simply detecting the sign of the skewness of the distribution." Col. 4, lns. 46–50.

As described above, Huynh et al. concerns the measurement of the roughness of a planar surface, a microscopic characteristic of material related to the average levelness of a surface. Further, the "surface flaw" analysis disclosed by Huynh et al. is used only to detect, not measure, surface flaws. Moreover, surface flaws are detected using a "skewness" value that is a function of both surface flaws and surface roughness. Thus, the analysis disclosed in Huynh et al. does not measure surface flaws independent of other surface characteristics.

Due to the limitations of the aforementioned technologies, the out-of-plane defects of paper ordinarily have been measured subjectively by individual inspection of paper samples. Although these subjective determinations are useful, they are inherently inconsistent and imprecise.

SUMMARY

The disclosed embodiments of the present method and apparatus address the shortcomings of the known prior art by providing a single objective value corresponding to the number and/or size of out-of-plane defects on a paper sample that can be easily and quickly determined. This single value may be used to determine whether paper is sufficiently free of out-of-plane defects and suitable for use in a particular application.

In an embodiment of the disclosed method, a paper sample is provided and illuminated with light at an angle greater than zero and less than ninety degrees, and typically less than twenty degrees. Light scattering resulting from light incident on the sample is determined at a plurality of measuring regions on the sample. An out-of-plane defect is determined from the light scattering by assigning the measuring regions to bands, calculating a standard deviation of light scattering for each of the bands, and averaging the standard deviations of the bands. Although visible light has been used with working embodiments, other light (e.g., UV, infrared, etc.) may be used.

In another embodiment, the measuring regions are assigned to multiple columns of the sample, and an out-of-plane defect value is determined for each column. The median of the out-of-plane defect values of the columns is calculated to determine a median out-of-plane defect value. The average of the out-of-plane defect values of the columns also may be calculated to determine an average out-of-plane defect value.

In another embodiment, an out-of-plane defect value is calculated for a sample and used to determine whether the paper sample satisfies certain predetermined criteria.

In another embodiment, the method for determining an out-of-plane defect value is encoded as a computer program.

In another embodiment, the above embodiments are used to determine a single streak defect value indicative of streaking on a paper sample.

Additional features of the method may include one or more of the following: defining the bands in one particular direction of the sample; using a digital camera or other charge coupled device to determine the light scattering; using a computer system to compute the out-of-plane defect value; using a lens (such as a Fresnel lens) to align the light incident on the sample; using a linear light source to illuminate the sample; using a fluorescent light source to illuminate the sample; assigning the measuring regions to six bands; and assigning the measuring regions to 352 columns having 272 measuring regions in each column.

One disclosed embodiment of the apparatus includes a housing that holds a paper sample and excludes ambient light. A light source is positioned within the housing and is configured to illuminate the sample at an angle greater than zero and less than ninety degrees. An image-capturing device for imaging light scattering on the sample is positioned in the housing. A computer analysis system can be used in combination with the apparatus to receive and analyze light scattering and compute an out-of-plane defect value. The computer analysis system may be configured to compute an out-of-plane defect value by assigning measuring regions to plural bands, calculating a standard deviation of light scattering for each of the bands, and averaging standard deviations of the bands. The computer analysis may be further configured to assign the measuring regions to plural columns, determine the out-of-plane defect value for each of the columns, and calculate a median of the out-of-plane defect values of the columns to determine a median out-of-plane defect value. The computer analysis system also may be configured to average the out-of-plane defect values of the columns to determine an average out-of-plane defect value.

In other embodiments, the image-capturing device may be a digital camera or charge coupled device, which may be positioned along an axis perpendicular to the plane of the sample. The housing may include a slidable stage attached to the housing and configured to hold the sample. A lens, such as a Fresnel lens, may be positioned inside the housing and used for aligning the light illuminating the sample. The light may be from a linear and/or fluorescent light source.

In another embodiment, a system for measuring out-of-plane defects in a paper sample is disclosed that includes an image capturing system and a computer analysis system. The computer analysis system may be configured to perform embodiments of the method described above.

Further features and advantages of the disclosed technology will become apparent with reference to the following detailed description and accompanying drawings.

DETAILED DESCRIPTION

The present method and apparatus are described below with reference to representative, nonlimiting embodiments. Flow charts are provided to explain certain features of the subject method. Although the various embodiments are described as useful for measuring out-of-plane defects of a paper sample, they may be used to determine out-of-plane defects present in any material having a desirably flat surface.

Figure 1:
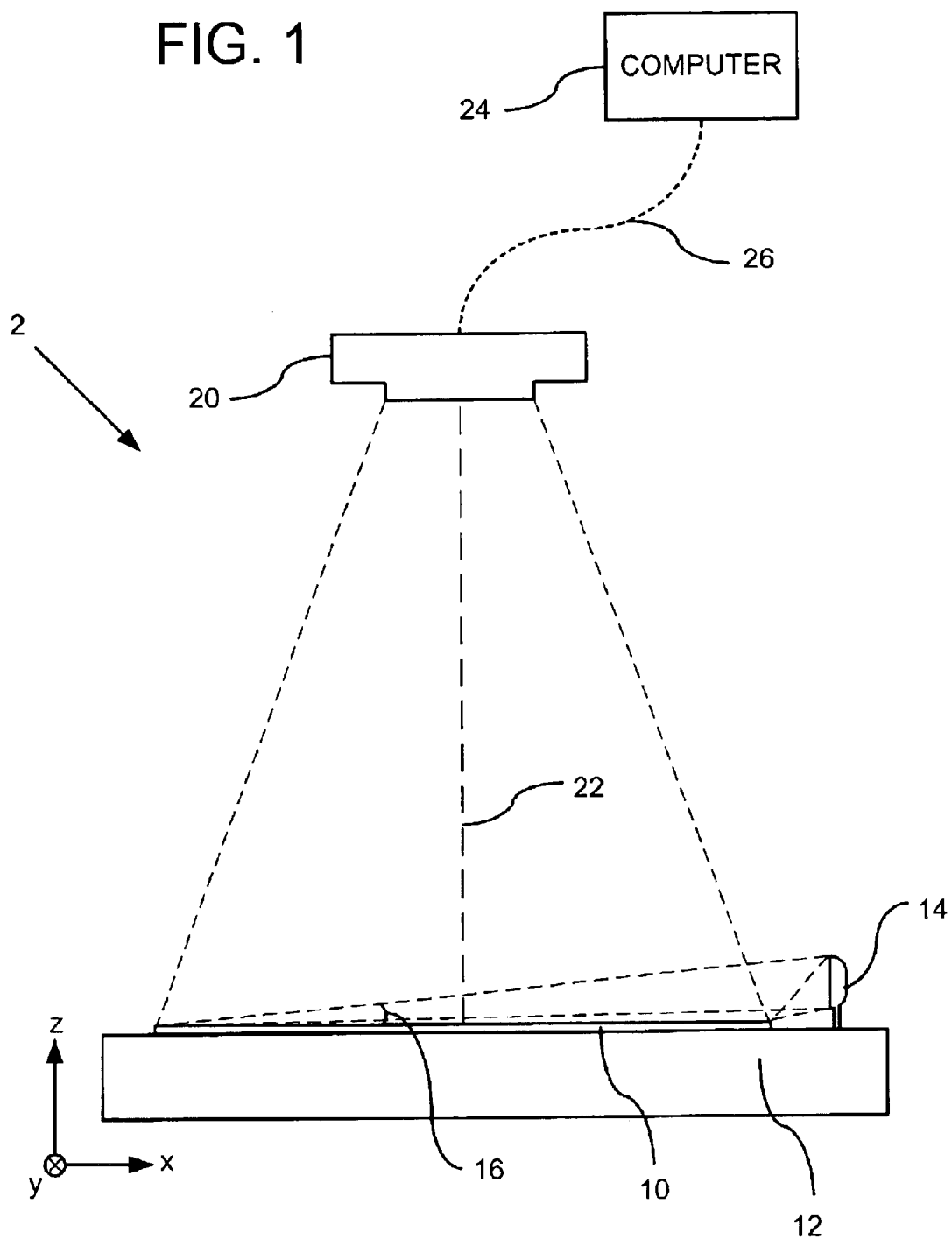
FIG. 1 is a schematic view depicting a representative embodiment of a system for determining out-of-plane defects in a paper sample.

FIG. 1 is a schematic view depicting a representative embodiment of system 2 for testing a paper sample 10 for out-of-plane defects. The paper sample 10 is positioned on a support 12. In one embodiment, paper sample 10 is analyzed for out-of-plane defects after the drying process of paper manufacturing has been completed and before any surface treatment is applied.

For purposes of this disclosure, paper sample 10 is referred to has having two dimensions of interest: a machine direction (MD) and a cross direction (CD). The machine direction is the direction parallel to the movement of the paper web during paper formation, and the cross direction is the direction transverse to the movement of the paper web. Alternatively, the paper may be referred to as having a first and a second direction. The specification of the dimensions is for exemplary purposes only and is not intended to be limiting in any way.

As further illustrated by FIG. 1, the sample 10 is illuminated by a light source 14 at an angle 16. Generally, angle 16 may be greater than zero but less than ninety degrees. In one embodiment, the angle 16 is less than twenty degrees so that out-of-plane defects cast discernible shadows and/or cause identifiable light scattering. In general, as the angle of incidence 16 decreases, the visible definition of the out-of-plane defects increases. At some angle approaching zero degrees, however, the quality of the light scattering image is compromised.

In one embodiment, light source 14 is a linear source positioned along the cross direction of the paper. Light source 14 may produce light of any wavelength, but in one working embodiment produces visible light (i.e. electromagnetic waves ranging from about 400 nm to 700 nm). Further, light source 14 may be one of several types. In a working embodiment, the light source 14 provided a uniform light substantially free from any point sources or "hot spots." A fluorescent light is used in one embodiment to produce such light.

The light may be filtered through a lens that aligns the light illuminating the paper sample 10. A Fresnel lens positioned between the light source 14 and the sample 10 was used in a working embodiment.

An image-capturing device 20 is positioned at a distance from the sample 10 and configured to image the light scattering caused by the interaction between the out-of-plane defects and the incident light. In one embodiment, the sample 10 is placed parallel to an XY-plane and the device 20 is positioned along an axis 22 parallel to the Z axis. In this embodiment, the device 20 is placed at a distance great enough to for the entire sample 10 to be imaged.

The image-capturing device 20 may be any device capable of imaging light scattering at multiple measuring regions and converting the light scattering into digital data. In one embodiment, the device 20 is a digital camera or a charge coupled device (CCD). A CCD is an integrated circuit comprising light-sensitive diodes that can convert various levels of red, green, and blue (RGB) light or various shades of black and white (gray scale) light at multiple measuring regions of an image (pixels) into corresponding electrical charges. The various RGB or gray-scale levels are transformed into digital data using an analog/digital (A/D) converter, which converts the electrical charge corresponding to the RGB or gray-scale level of each pixel into a digital value representing the intensity of the signal (e.g., from 0 to 255).

In one embodiment, a measuring region of the paper sample 10 corresponds to a pixel of the digital camera or CCD. Thus, the maximum number of measuring regions possible is determined by the resolution of the digital camera or CCD. In other embodiments, however, a measuring region of the sample 10 may correspond to multiple pixels of the digital camera or CCD, or to other specified areas.

In alternative embodiments, other image-capturing devices, such as cameras using photosensitive film, may be used to image the light scattering on the surface of the sample 10. The use of non-digital devices, however, requires the resulting image to be digitized before being analyzed for out-of-plane defects (e.g., by use of a digital scanner).

When the light scattering is being imaged by the device 20, it is desirable to eliminate light from other sources. Accordingly, for example, the imaging may be performed in a dark room or housing. For example, the entire imaging system may be placed inside an enclosure that substantially eliminates ambient light.

As shown in FIG. 1, a computer analysis system 24 may be configured to receive the light-scattering information and execute a program to determine an out-of-plane defect value through a series of calculations. The computer system 24 is connected to the image-capturing device 20 via connection 26, which may be any suitable connection. In one embodiment, connection 26 is a physical connection, such as a computer wire. In another embodiment, connection 26 is a non-physical connection, such as an infrared or RF connection. In another embodiment, connection 26 may be through a memory storage device, such as a floppy disk, that is transferable between device 20 and system 24.

System 2 may be modified to detect out-of-plane defects on a continuous paper web. The necessary modifications may include using high-speed cameras, strobe lighting, and a high-speed paper positioning devices for properly orienting the moving web with respect to the light and camera.

Figure 2:
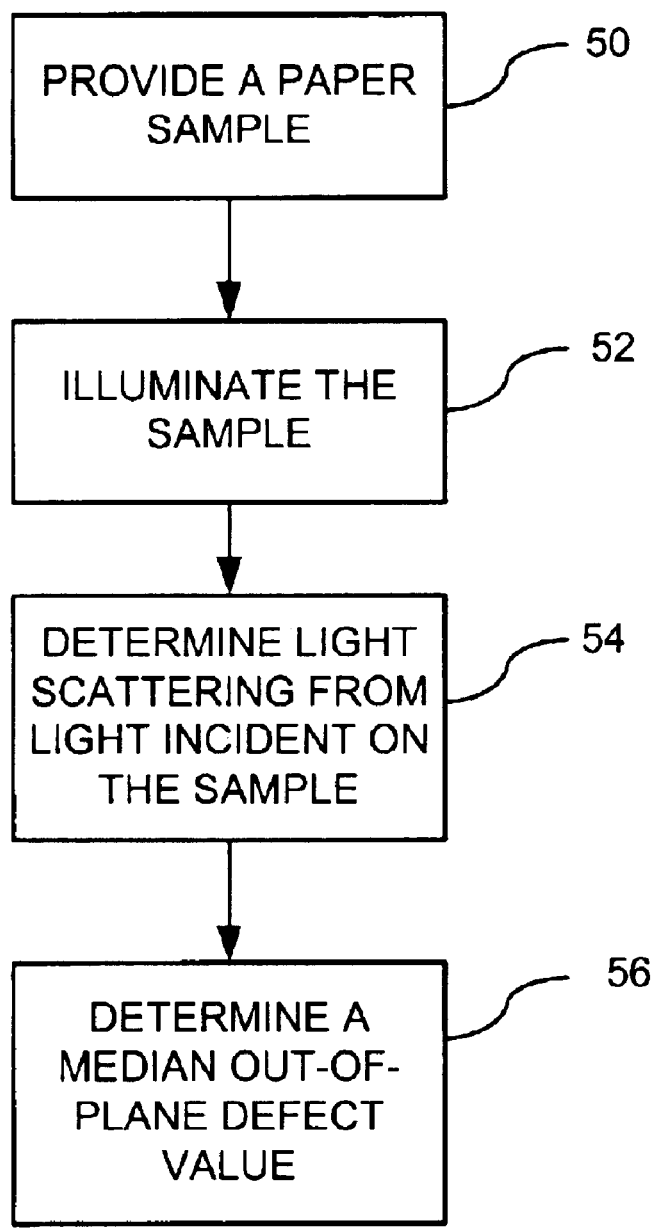
FIG. 2 is a flowchart depicting a representative embodiment of a method for determining an out-of-plane defect value in a paper sample.

FIG. 2 is a flowchart depicting a representative embodiment of the method for measuring out-of-plane defects. In process block 50, a paper sample is provided. In process block 52, the paper sample is illuminated with light at an angle greater than zero but less than ninety degrees. The light may be from a source such as the filtered fluorescent light discussed above. In process block 54, light scattering resulting from the light incident on the sample is determined at multiple measuring regions on the sample. The light scattering may be determined by imaging the paper sample using an image-capturing device, such as the ones discussed above capable of converting light scattering into digital data. In process block 56, a median out-of-plane defect value is determined. The median out-of-plane defect value may be determined using a computer analysis system.

Figure 3:
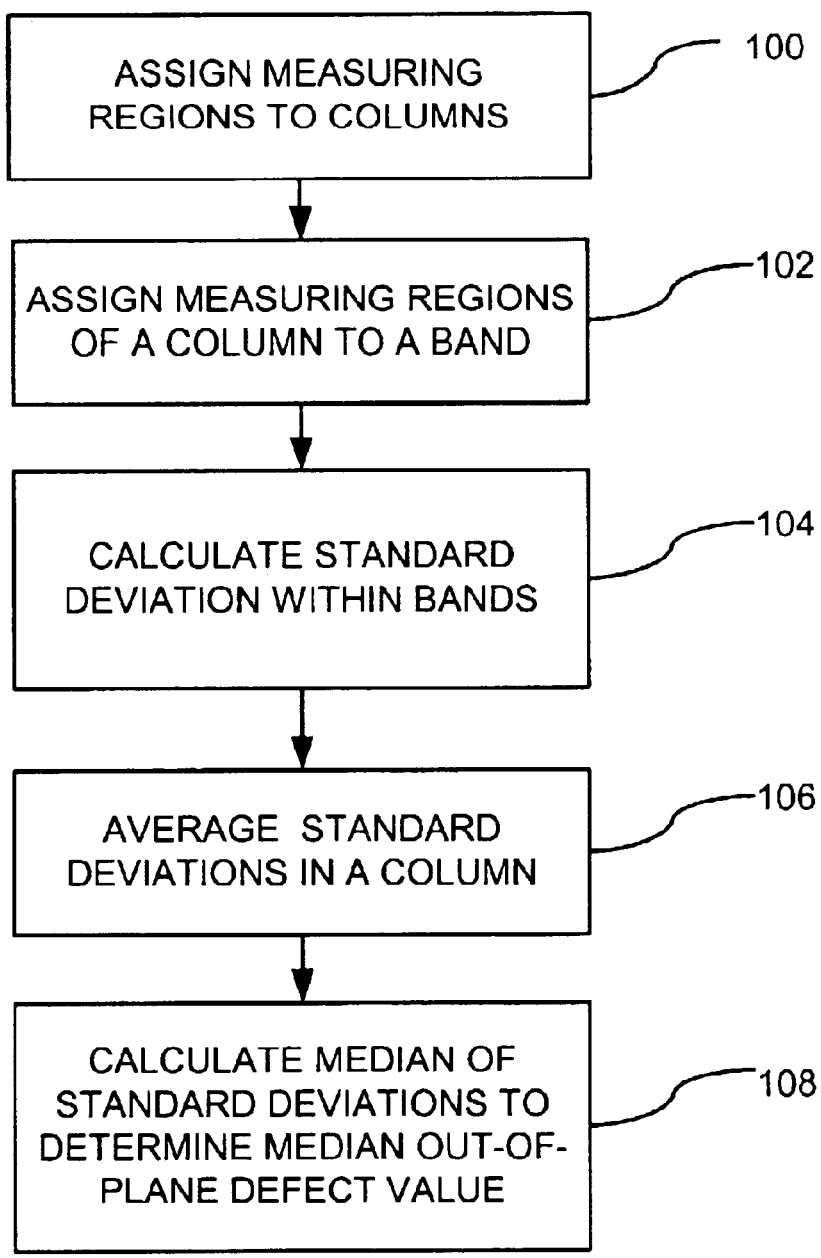
FIG. 3 is a flowchart depicting the analytical processes used to calculate the out-of-plane defect value according to the method of FIG. 2.
Figure 4:
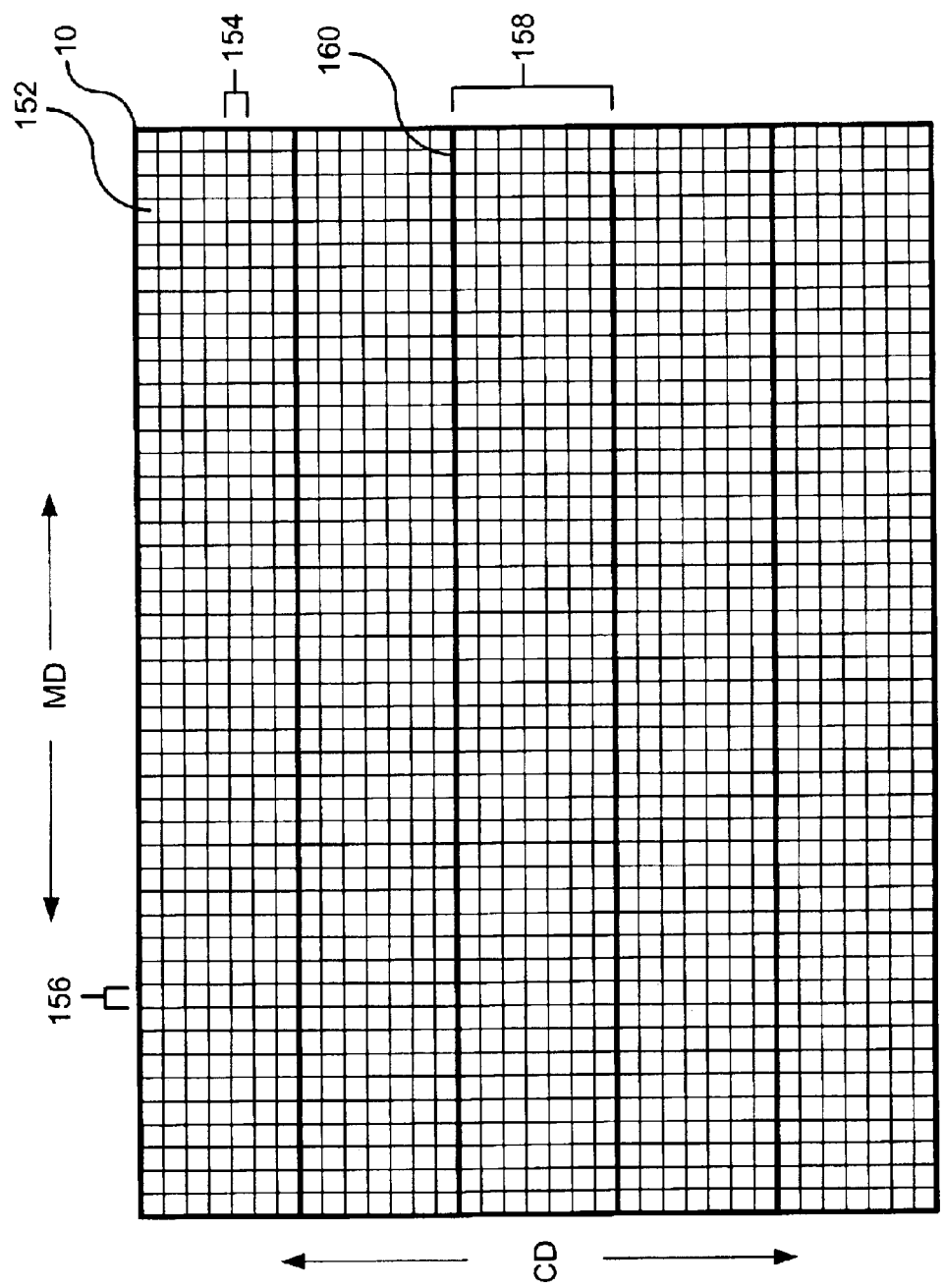
FIG. 4 is a schematic depiction of various subdivisions of a paper sample used to determine out-of-plane defects according to a representative embodiment.

FIG. 3 is a flowchart that depicts the steps for determining a median out-of-plane defect value during process block 56 of FIG. 2. Reference also is made to FIG. 4, which schematically shows paper sample 10, along with various exemplary subdivisions of the sample that are useful for determining the median out-of-plane defect value.

In FIG. 4, the entire surface of the paper sample 10 is segmented into multiple measuring regions 152. As noted above, the measuring regions 152 in one embodiment correspond to the resolution of the digital camera or CCD being used to image the sample 10. The measuring regions 152, however, may correspond to combinations or averages of multiple pixels of the digital camera or CCD. At this point in the process, each measuring region 152 has had a light-scattering value, corresponding to the RGB or gray-scale value, determined at process block 54 of FIG. 2.

In process block 100, measuring regions 152 are assigned to columns, shown generally at 156. A column 156 extends along a first direction of the paper sample 10, such as the cross direction, and comprises all the measuring regions 152 along that direction for a certain width. In one embodiment, shown in FIG. 4, column 156 has a width of one measuring region 152. Alternatively, however, column 156 may have a width of any number of measuring regions 152, including a width equal to the entire length of a second direction, such as the machine direction, of the sample 10.

The number of columns 156 will vary depending on the number of measuring regions 152 available. In one embodiment, for instance, the measuring regions 152 are assigned to 352 columns, each column containing 272 measuring regions., In process block 102, the measuring regions 152 of a column 156 are assigned to multiple bands, shown generally at 158 by the horizontal lines 160 in FIG. 4. A band 158 divides a column 156 into groups of multiple measuring regions 152. In one embodiment, as is shown in FIG. 4, the bands 158 divide the measuring regions 152 of the columns 156 into groups of evenly distributed rows, shown generally at 154. Bands 158 preferably remain as uniform as possible along the first direction of the sample 10 (the machine direction in FIG. 5). For example, in an embodiment having 352 columns and 272 rows, six bands are assigned, wherein the first and sixth band contain forty-six rows and the second through fifth bands contain forty-five rows.

In process block 104, the standard deviations of the RGB or grey-scale values among the measuring regions 152 of each band 158 are calculated for each column 156. Thus, for each band 158 in a column 156, a separate standard deviation is determined. For example, in an embodiment having 352 columns and six bands, this process results in six standard deviations for each of the columns.

In process block 106, the standard deviations of the bands 158 are averaged for each column 156. Thus, for each column 156, a separate average is determined. This average value is termed the "out-of-plane defect value" for the respective column 156. For example, in an embodiment having 352 columns and six bands, this process results in the determination of 352 out-of-plane defect values.

In process block 108, a median value for the out-of-plane defect values is calculated using the out-of-plane defect values from each column 156. The resulting value is termed the "median out-of-plane defect value." In the embodiment having 352 columns and six bands, this process determines the median of 352 out-of-plane defect values. The median out-of-plane defect value is a single value that can be used to evaluate the out-of-plane defects in a paper sample 10.

In the embodiment wherein the width of the column 156 extends across the entire length of the sample 10, no median out-of-plane value need be calculated. Instead, the out-of-plane value calculated in process block 106 is the single value that can be used to evaluate out-of-plane defects in a paper sample 10. In this embodiment, process block 56 in FIG. 2 corresponds to determining an out-of-plane defect value.

In an alternative embodiment, an average value of the out-of-plane defect values can be calculated to determine an "average out-of-plane defect value." The average out-of-plane defect value is also a single value that can be used to evaluate the out-of-plane defects in a paper sample 10.

In the embodiments of the method described above, the out-of-plane defect values increase as the number and/or the size of the out-of-plane defects in a paper sample 10 increases. One of ordinary skill in the art can modify the procedures, however, such that the out-of-plane defect values change in different ways when the number and/or size of out-of-plane defects increases.

Further, the embodiments of the method described above may be used to determine a single streak defect value. The streak defect value corresponds to the number and/or size of streaking defects caused during the paper-making process.

Any of the out-of-plane defect values described above can be used during paper manufacturing to determine whether a paper sample 10 from a paper roll satisfies a certain predetermined criteria depending on the application for which the paper is being manufactured. Because the paper may be evaluated before any treatment process, paper that does not satisfy the criteria can be recycled without further costly treatment. Further, any of the out-of-plane defect values described above may be used to evaluate whether adjustments should be made to the machinery or paper-making process, and whether any such changes made during paper manufacture, result in improved surface characteristics of the paper.

Figure 5:
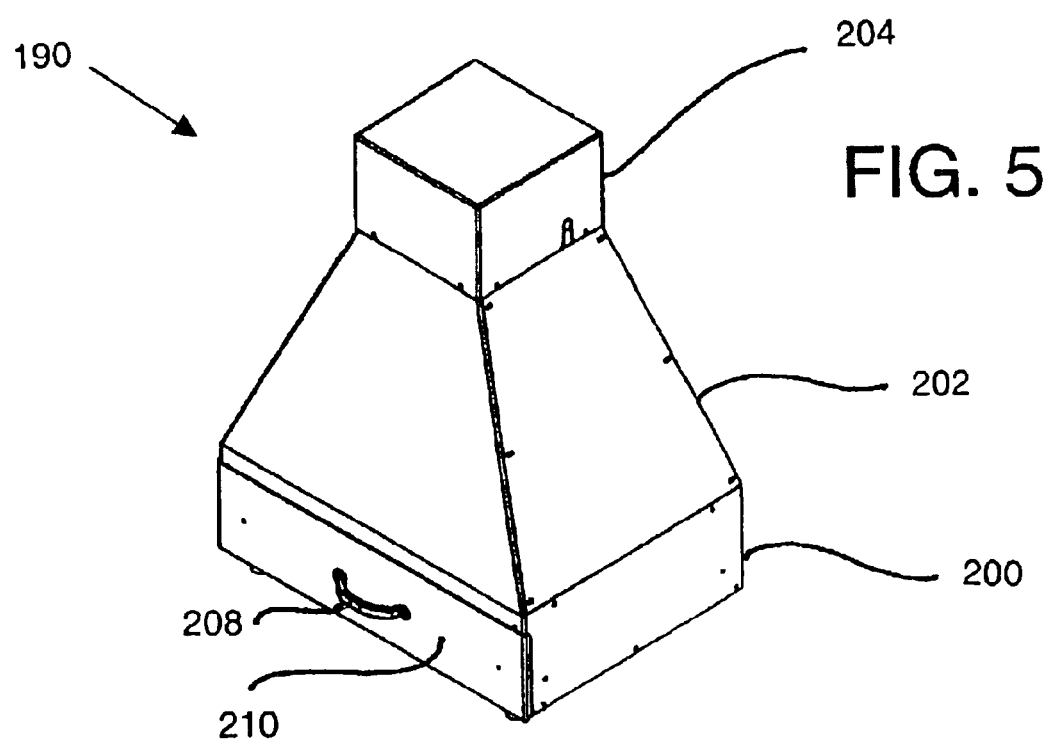
FIG. 5 is a perspective view of a housing for holding a paper sample according to one embodiment of a disclosed apparatus.

FIG. 5 is a perspective view of a housing 190 for holding a paper sample 10 (not shown) according to a representative embodiment. A sample-holding portion 200 is configured to hold and illuminate the sample 10 with a light source 220 (not shown) mounted to the portion 200. The sample-holding portion 200 further comprises a stage 210 that is configured to slide into and out of the housing 190 and is described below. A handle 208 is connected to the sample-holding portion 200 for moving the portion into and out of the housing 190.

A hood 202 is connected to the sample-holding portion 200. Hood 202 is configured to substantially exclude ambient light from sources outside the housing 190. Hood 202 may be constructed from any suitable material, but in one embodiment is constructed from aluminum sheet metal.

An imaging-device housing 204 is connected to the hood 202 and is configured to hold an imaging device, such as the digital camera discussed above. In one embodiment, the imaging-device housing 204 is configured to orient a lens of the imaging device toward the paper sample 10 along an axis perpendicular to the surface of the sample and at a distance from the sample such that the sample's entire surface may be imaged. The imaging-device housing 204 may be constructed from any suitable material, but in one embodiment is constructed from aluminum sheet metal.

The interior of the housing 190 may be covered with a non-reflective material to prevent reflected light from illuminating the paper sample 10 at undesirable angles, reducing the quality of the image produced. For instance, in one embodiment, the interior of the housing 190 is painted with flat black paint.

Figure 6:
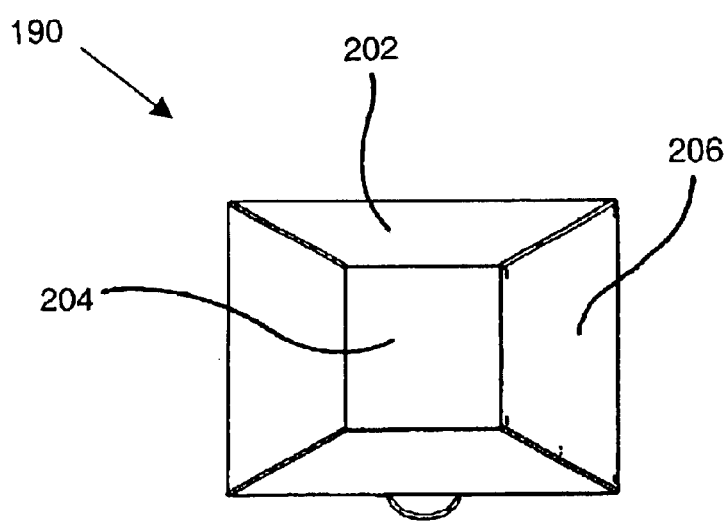
FIG. 6 is a plan view of the housing in FIG. 5.

FIG. 6 is a plan view of the housing. Hood 202 is described above is shown. Hood 202 further comprises a removable side 206 that forms one side of the hood and is removably attached to the hood. Removable side 206 may be detached from hood 202 so that the interior of the housing 190 may be accessed and serviced if necessary. In another embodiment, hood 202 does not have any removable sides.

Figure 7:
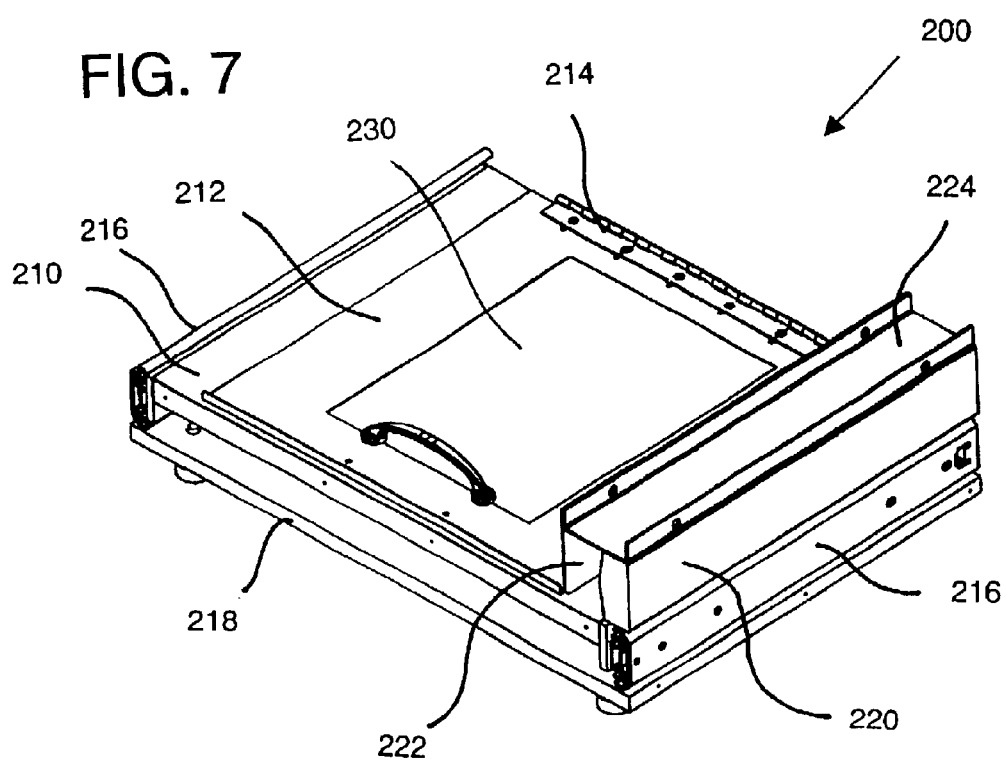
FIG. 7 is a perspective view of the sample-holding portion of the housing in FIG. 5.

FIG. 7 is a perspective view of the sample-holding portion 200 illustrated in FIGS. 5 and 6. Stage 210 is connected to a base 218 via an assembly 216, discussed more fully below. Base 218 comprises multiple feet 232 for supporting the base 218 and, in one embodiment, attenuating vibration. Stage 210 further comprises a sample-positioning door 212 connected to the stage via a continuous hinge 214. Door 212 holds the paper sample 10 (not shown) in a single desirable position so that it may be optimally imaged. Door 212 defines a portion for retaining a translucent window 230 that allows light to illuminate the sample 10.

In one alternative embodiment, the door 212 may be removed from the stage 210 so that the paper sample 10 lies unobstructed on the stage. Other alternative means for positioning the paper sample 10 on the stage 210 may be utilized, such as fasteners located at the four corners of the sample, positioning ridges formed into the stage, or adhesive materials placed on the stage.

A light source 220 is connected to the base 210 via the hood 202 (not shown). In one embodiment, the light source 220 is a linear fluorescent light source positioned adjacent the paper sample 10 such that the sample is illuminated along its cross direction. Additionally, as more fully discussed above, the light source 220 is positioned to create light having a low angle of incidence with the sample 10.

A lens 222 is connected to the light source 220 and the hood 202 via a support 224. A number of different lenses 222 may be used to filter and shape the light of the light source 220. In one embodiment, a lens 222, such as a Fresnel lens, is used to align the light in a uniform direction onto the paper sample 10. In another embodiment, no lens is placed between the light source 220 and the paper sample 10.

Figure 8:
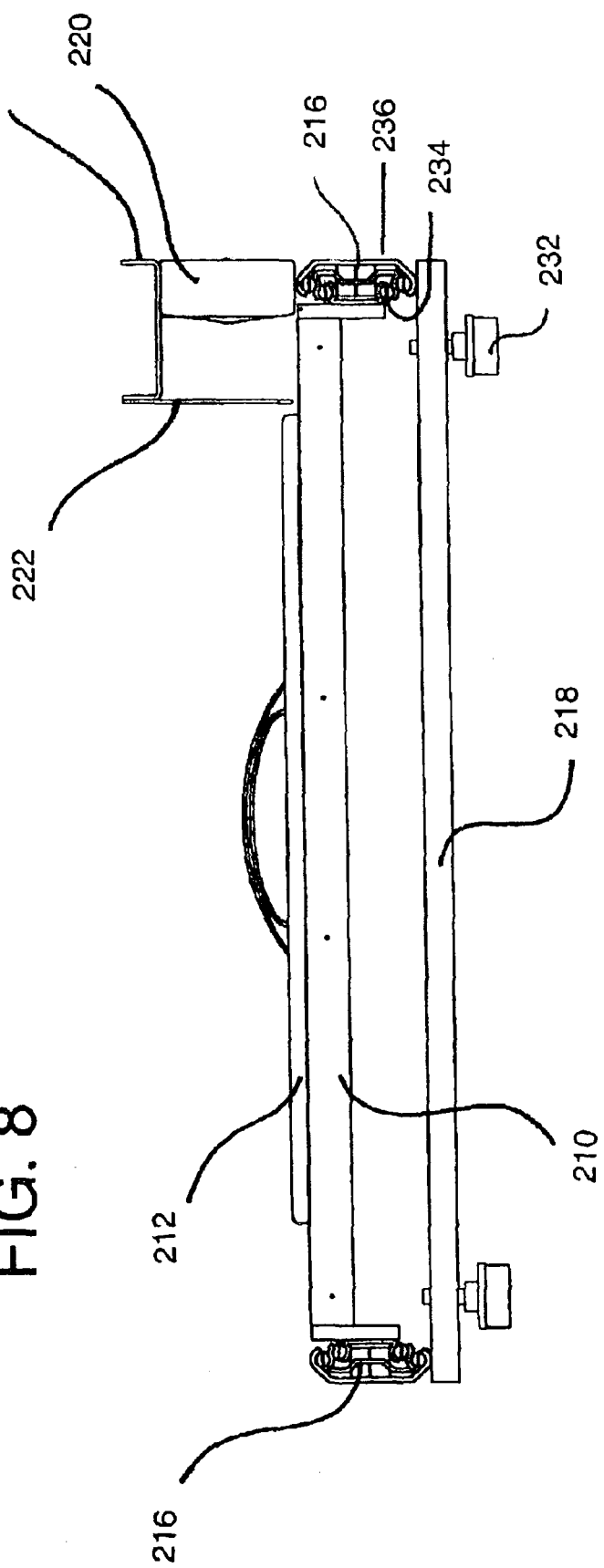
FIG. 8 is a front view of the sample-holding portion of the housing in FIG. 5.

FIG. 8 is a front view of the sample-holding portion 200 showing the same features discussed above with respect to FIG. 7. Assembly 216 is shown further comprising an inner portion 234 connected to the stage 210 and an outer portion 236 connected to the base 218. This configuration allows the inner portion 234 to slide on bearings (not shown) along a path defined by the outer portion 236.

EXAMPLE 1

The following example is provided to exemplify certain features of the disclosed embodiments of the described method and apparatus. The scope of the invention should not be limited those features exemplified.

This example describes a process for analyzing a paper sample using the apparatus and method described herein. A housing as described above having a linear fluorescent light source and a Fresnel lens was used to analyze a paper sample made by a commercial paper-making process and machine. A paper sample having dimensions of 11 inches along its machine direction and 8.5 inches along its cross direction was positioned on the stage of the sample-holding portion of the housing. Light from the linear fluorescent light source was used to illuminate the paper sample at an angle substantially equal to two degrees. Light scattering was digitally imaged using a Kodak EDAS 290 imaging device at a resolution of 1200×1792 pixels. The light-scattering information was then analyzed by a computer implementing the steps of FIGS. 2 and 3. In the analysis, the pixels were assigned to 95,744 measuring region, 352 columns, 272 rows, and six bands. A median out-of-plane defect value of 7.1 was determined. This process was repeated several times to provide plural median out-of-plane defect values for plural paper samples. The out-of-plane defect values of the paper samples ranged from 0 to 200, but were most likely greater than zero to less than 15. Zero represents the lowest median out-of-plane defect value possible and indicates that a sample has no measurable out-of-plane defects. These paper samples were then evaluated by several individuals to provide subjective rankings of paper quality. These subjective rankings were found to agree with the objective median out-of-plane defect values determined by the disclosed method.

Whereas the disclosed method and apparatus has been described in connection with multiple representative embodiments, it will be understood that the disclosed technology is not limited to those embodiments. On the contrary, the disclosed technology is intended to encompass all modifications, alternatives, and equivalents as may be included within the spirit and scope of the disclosed method and apparatus, as defined by the appended claims.

What is claimed is:

1. A method for determining out-of-plane defects in a paper sample, comprising:
   providing a paper sample having a first direction and a second direction;
   illuminating the sample with light at an angle greater than zero and less than 90 degrees;
   determining light scattering resulting from light incident on the sample at a plurality of measuring regions defined in the first and second directions of the sample; and
   determining an out-of-plane defect value by assigning the measuring regions to plural bands, calculating a standard deviation of light scattering for each of the bands, and averaging standard deviations of the bands.

2. The method according to claim 1 further comprising:
   assigning the measuring regions to plural columns defined in the first direction of the sample;
   determining the out-of-plane defect value for each of the columns; and
   calculating the median of the out-of-plane defect values of the columns to determine a median out-of-plane defect value.

3. The method according to claim 2, further comprising averaging the out-of-plane defect values of the columns to determine an average out-of-plane defect value.

4. The method according to claim 2, where determining light scattering includes using a digital camera or charge coupled device, and a maximum number of measuring areas is determined by resolution of the digital camera or charge coupled device.

5. The method according to claim 2, where there are 352 columns in the first direction of the sample and 272 measuring regions in each column.

6. The method according to claim 1, where the bands are defined along the second direction of the sample.

7. The method according to claim 1, where determining light scattering includes imaging the light scattering.

8. The method of claim 7, where imaging comprises using a digital camera or charge coupled device.

9. The method according to claim 1, where determining an out-of-plane defect includes using a computer system configured to compute the out-of-plane defect value.

10. The method according to claim 1, where light incident on the sample is at an angle greater than zero and less than twenty degrees.

11. The method according to claim 1, where light incident on the sample is visible light.

12. The method according to claim 1, where light incident on the sample is aligned in a single direction by a lens.

13. The method according to claim 1, where light incident on the sample is from a linear light source.

14. The method according to claim 13, where light incident on the sample is from a fluorescent light source.

15. The method according to claim 1, where the number of bands depends on the number of measuring regions available.

16. The method according to claim 1, where the number of bands is six.

17. A method for evaluating out-of-plane defects, comprising:
   providing a paper sample; and
   evaluating whether the sample satisfies a predetermined criteria using an out-of-plane defect value, the out-of-plane defect value being obtained by illuminating the sample with light at an angle greater than zero and less than 90 degrees, determining light scattering resulting from light incident on the sample at a plurality of measuring regions defined in the first and second directions of the sample, and determining an out-of-plane defect value by assigning the measuring regions to plural bands, calculating a standard deviation of light scattering for each of the bands, and averaging standard deviations of the bands.

18. A computer program encoding a method for determining out-of-plane defects in a paper sample comprising:
   compiling light-scattering data resulting from light incident on the sample at a plurality of measuring regions; and
   determining an out-of-plane defect value from compiled data by assigning the measuring regions to plural bands, calculating a standard deviation of light scattering for each of the bands, and averaging the standard deviations of the bands.

19. A computer programmed with the computer program of claim 18.

20. A method for measuring streak defects in a paper sample, comprising:
   providing a paper sample having a first and a second direction;
   illuminating the sample with light at an angle greater than zero and less than 90 degrees;
   determining a single streak defect value by analyzing light scattering resulting from light incident on the sample at a plurality of measuring regions defined in the first and second directions of the sample and determining a streak defect value by assigning the measuring regions to plural bands, calculating a standard deviation of light scattering for each of the bands, and averaging standard deviations of the bands.

21. The method according to claim 20, where determining the single streak defect value further comprises:

assigning the measuring regions to plural columns defined along the first direction of the sample;

determining the streak defect value of each of the columns; and calculating the median of the streak defect values of the plural columns to determine a single streak defect value.

22. The method according to claim 21, wherein the single streak defect value is calculated by averaging the streak defect values of the columns.

23. The method according to claim 20, where the light is visible light.

24. The method according to claim 20, where light incident on the sample is aligned in a single direction by a lens.

25. The method according to claim 20, where the light is from a linear light source.

26. The method according to claim 20, where the light is from a fluorescent light source.

27. The method according to claim 20, where illuminating is performed at an angle greater than zero and less than twenty degrees.

28. The method according to claim 20, where the bands are defined along the second direction of the sample.

29. The method according to claim 20, where determining light scattering includes imaging the light scattering.

30. The method of claim 29, where imaging comprises using a digital camera or charge coupled device.

31. The method according to claim 20, where determining a streak defect value includes using a computer system capable of analyzing light scattering.

32. The method according to claim 20, where determining light scattering includes using an imaging device, and a maximum number of measuring areas is determined by resolution of the imaging device.

33. The method of claim 32, where the imaging device is a digital camera or charge coupled device.

34. The method according to claim 20, where the number of bands depends on the number of measuring regions available.

35. The method according to claim 20, where the number of bands is six.

36. The method according to claim 20, where the method is a batch method.

37. The method according to claim 20, where the method is continuously performed on a travelling web.

38. An apparatus, comprising:

a housing for holding a paper sample;

a light source positioned within the housing configured to illuminate the sample at an angle greater than zero and less than 90 degrees;

an image-capturing device for imagine light scattering on the sample in order to measure an out-of-plane defect; and a computer analysis system operably coupled to the image-capturing device and configured to analyze light scattering data and compute an out-of-plane defect value by assigning measuring regions to plural bands, calculating a standard deviation of light scattering for each of the bands, and averaging standard deviations of the bands.

39. The apparatus of claim 38, where the paper sample has a first direction and a second direction, and the computer analysis system is further configured to assign the measuring regions to plural columns defined in the first direction of the sample, determine the out-of-plane defect value for each of the columns, and calculate the median of the out-of-plane defect values of the columns to determine a median out-of-plane defect value.

40. The apparatus of claim 39, where the computer analysis system is further configured to average the out-of-plane defect values of the columns to determine an average out-of-plane defect value.

41. The apparatus of claim 38, where the image-capturing device comprises a digital camera or charge coupled device configured to image the light scattering.

42. The apparatus of claim 38, where the image-capturing device is positioned along an axis perpendicular to a plane of the sample.

43. The apparatus of claim 38, where the housing comprises a stage slidably attached to the housing and configured to hold the sample.

44. The apparatus of claim 38 further comprising a lens positioned within the housing and configured to filter and align the light illuminating the sample.

45. The apparatus of claim 38, where the light source is a linear light source.

46. The apparatus of claim 38, where the light source is a fluorescent source.

47. A system for measuring out-of-plane defects in a paper sample having a first and a second direction comprising:

an image capturing system configured to obtain light-scattering information resulting from light incident on the sample at a plurality of measuring regions defined in the first and second directions of the sample; and a computer analysis system configured to receive the light-scattering information and determine an out-of-plane defect value by assigning the measuring regions to plural bands, calculating a standard deviation of light scattering for each of the bands, and averaging standard deviations of the bands.

48. The system of claim 47, where the computer analysis system is further configured to determine an out-of-plane defect value by assigning the measuring regions to plural columns defined in the first direction of the sample, determining the out-of-plane defect value for each of the columns, and calculating the median of the out-of-plane defect values of the plural columns to determine a median out-of-plane defect value.

49. The system of claim 48, where the computer analysis system is further configured to average the out-of-plane defect values of the columns to determine an average out-of-plane defect value.

50. The system of claim 47, where the bands are defined along the second direction of the sample.

* * * * *

UNITED STATES PATENT AND TRADEMARK OFFICE
CERTIFICATE OF CORRECTION

| | | |
|---|---|---|
| PATENT NO. | : 6,947,150 B2 | Page 1 of 1 |
| APPLICATION NO. | : 10/324206 | |
| DATED | : September 20, 2005 | |
| INVENTOR(S) | : Rucker et al. | |

It is certified that error appears in the above-identified patent and that said Letters Patent is hereby corrected as shown below:

Column 6, line 48, "regions.," should be --regions.--.

Column 11, line 51, "imagine" should be --imaging--.

Signed and Sealed this

Twenty-first Day of August, 2007

JON W. DUDAS
*Director of the United States Patent and Trademark Office*